US008592695B2

(12) United States Patent
Las Navas Garcia

(10) Patent No.: US 8,592,695 B2
(45) Date of Patent: Nov. 26, 2013

(54) STACKABLE CRUCIBLE, A SYSTEM USING A STACKABLE CRUCIBLE, AND A METHOD OF USING A STACKABLE CRUCIBLE

(76) Inventor: Jose Maria Las Navas Garcia, Conway, SC (US)

( * ) Notice: Subject to any disclaimer, the term of this patent is extended or adjusted under 35 U.S.C. 154(b) by 501 days.

(21) Appl. No.: 12/956,229

(22) Filed: Nov. 30, 2010

(65) Prior Publication Data

US 2012/0132472 A1    May 31, 2012

(51) Int. Cl.
| | |
|---|---|
| *G01G 19/00* | (2006.01) |
| *G01G 21/00* | (2006.01) |
| *G01G 21/28* | (2006.01) |
| *G01N 31/00* | (2006.01) |
| *G01N 25/00* | (2006.01) |
| *B65D 6/00* | (2006.01) |
| *B65D 13/02* | (2006.01) |

(52) U.S. Cl.
USPC ............ 177/1; 422/63; 422/78; 422/547; 422/908; 206/506; 220/4.06; 220/4.07; 220/4.26; 177/126; 177/145; 177/245; 374/14

(58) Field of Classification Search
USPC ............ 374/14; 422/63–65, 78, 547, 908; 206/506, 519, 520; 220/4.06, 4.07, 220/4.26, 4.27; 177/1, 145, 245, 50, 126; 73/1.13, 1.15
See application file for complete search history.

(56) References Cited

U.S. PATENT DOCUMENTS

| | | | | | |
|---|---|---|---|---|---|
| 3,190,731 | A | * | 6/1965 | Weiskopf | 422/557 |
| 3,592,277 | A | * | 7/1971 | Ackeret | 177/126 |
| 3,894,591 | A | * | 7/1975 | Ackeret | 177/126 |
| 4,248,315 | A | * | 2/1981 | Falinower | 177/50 |
| 4,456,580 | A | * | 6/1984 | Yamada et al. | 422/63 |
| 4,559,201 | A | * | 12/1985 | Yamada et al. | 422/63 |
| 4,846,292 | A | * | 7/1989 | Narukawa | 177/50 |
| 5,064,009 | A | * | 11/1991 | Melcher et al. | 177/245 |
| 5,441,891 | A | * | 8/1995 | Burkovich et al. | 436/48 |
| 5,658,532 | A | * | 8/1997 | Kurosaki et al. | 422/64 |
| 5,670,120 | A | * | 9/1997 | Degenhardt et al. | 422/561 |
| 6,117,391 | A | * | 9/2000 | Mootz et al. | 422/65 |
| 7,048,888 | B2 | * | 5/2006 | Las Navas Garcia | 422/64 |
| 7,172,729 | B2 | * | 2/2007 | Las Navas Garcia | 422/78 |
| 7,402,280 | B2 | * | 7/2008 | Ford | 422/63 |
| 8,323,565 | B2 | * | 12/2012 | Ford | 422/63 |
| 2003/0003016 | A1 | * | 1/2003 | Las Navas Garcia | 422/63 |
| 2012/0058533 | A1 | * | 3/2012 | Biton et al. | 435/161 |

* cited by examiner

*Primary Examiner* — Randy W Gibson
(74) *Attorney, Agent, or Firm* — Epstein Drangel LLP; Robert L. Epstein

(57) ABSTRACT

A system is provided for analyzing a plurality of samples in a furnace. The system includes an upper holder including at least one opening adapted to engage at least one upper crucible. The system also includes a lower holder including at least one opening adapted to engage at least one lower crucible. The system includes a scale adapted to receive a lower crucible and weigh the lower crucible. The scale is further adapted to receive a combination of an upper crucible stacked on the lower crucible and weigh the combination. The system also includes means for moving the upper holder and the lower holder relative to each other and relative to the scale so that the scale selectively receives the lower crucible and the combination of the upper crucible stacked on the lower crucible. A method of testing samples in a furnace is provided.

16 Claims, 8 Drawing Sheets

STACKABLE CRUCIBLE, A SYSTEM USING A STACKABLE CRUCIBLE, AND A METHOD OF USING A STACKABLE CRUCIBLE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to crucibles, and in particular relates to stackable crucibles and systems for using stackable crucibles in furnaces.

2. Description of Prior Art

Thermogravimetric analyzers (TGA) are used to analyze moisture, volatiles and ash (coal and coke). Some systems have multi-sample capabilities and/or crucible covers for allow the analysis of several samples simultaneously. Automation and computer control allow increased productivity. Automatic crucible cover placement and removal during the analysis of volatiles makes the instrument fully automatic and reduces the risk of sample oxidation, while also providing better repeatability of the volatile matter results.

U.S. Pat. No. 7,048,888 to Las Navas Garcia discusses an automatic cover system for proximate analyzers and the like. An apparatus is provided to automatically cover and uncover crucibles according to a predetermined procedure in a proximate analyzer. A series of crucibles mounted in a first carousel is heated in a furnace. A second carousel mounted above the first carousel holds crucible covers. A mechanism synchronizes the movements of the carousels so that the heated crucibles are automatically covered and uncovered at the appropriate times during the analysis with a corresponding cover by lowering or raising the second carousel. The movements of both carousels are automatically controlled so that at appropriate points in the testing cycle they rotate simultaneously about a common central axis and a crucible is deposited on a weighing platform by controlling the vertical motion of the entire carousel apparatus. The crucible is weighed either with or without a crucible cover depending on the stage of the analysis without the need of manual intervention. The specification of U.S. Pat. No. 7,048,888 is incorporated herein by reference.

U.S. Pat. No. 7,172,729 to Las Navas Garcia discusses a mixed sample moisture or ash analyzer. In particular, an analyzer for moisture or ash testing is provided where a robotic arm retrieves a crucible and sample from a conveyor, inserts it into a small opening in the upper surface of the furnace chamber and deposits it in an aperture on a carousel located within the furnace chamber. The carousel in the furnace chamber manipulates the crucibles within the furnace chamber. The opening in the upper surface of the furnace chamber is positioned such that when the carousel is ready for loading or unloading, an aperture in the carousel for holding the crucibles is aligned with the opening. At appropriate points during the testing cycle, individual crucibles are automatically deposited on a weighing platform connected to an internal balance through vertical motion of the carousel. Once final weighing in the test cycle is performed, the crucible is removed through the opening on the upper surface of the furnace chamber by the same robot arm which placed it in the chamber. The specification of U.S. Pat. No. 7,172,729 is incorporated herein by reference.

BRIEF SUMMARY OF THE INVENTION

A system is provided for analyzing a plurality of samples in a furnace. The samples may be analyzed for moisture and/or ash in coal, coke or any other appropriate material. The system includes an upper holder including at least one opening adapted to engage at least one upper crucible. Each upper crucible has a wall and a bottom for enclosing a first sample. The system also includes a lower holder including at least one opening adapted to engage at least one lower crucible. Each lower crucible has a wall and a bottom for enclosing a second sample. The system includes a scale adapted to receive a lower crucible and weigh the lower crucible. The scale is further adapted to receive a combination of an upper crucible stacked on the lower crucible and weigh the combination. The system also includes a frame enclosing a furnace, the upper holder, the lower holder and the scale, and means for moving the upper holder and the lower holder relative to each other and relative to the scale so that the scale selectively receives the lower crucible and the combination of the upper crucible stacked on the lower crucible.

In the system, the upper holder may be an upper carousel and the lower holder may be a lower carousel, and the upper carousel and the lower carousel may be coaxial. The upper carousel and the lower carousel may rotate together. In the system, the means for moving the upper holder and the lower holder relative to each other and relative to the scale may includes means for moving at least one of the upper carousel and the lower carousel rotate axially with respect to the other of the upper carousel and the lower carousel. In the system, the openings of the upper carousel may be positioned away from a central axis, and the openings of the lower carousel may be positioned away from the central axis and are aligned vertically with the openings of the upper carousel.

The openings of the upper carousel may be positioned around an outer edge of the upper carousel, and the openings of the lower carousel may be positioned around an outer edge of the lower carousel.

In the system, the upper crucible may include a wall and a bottom for enclosing a first sample, and the upper holder may engage an outer perimeter of the wall of the upper crucible or a flange on the outer perimeter of the wall of the upper crucible. The lower crucible may include a wall and a bottom for enclosing a sample, and the lower holder may engage an outer perimeter of the wall of the lower crucible or a flange on the outer perimeter of the wall of the lower crucible.

In the system, the upper holder may engage an outer perimeter of the wall of the upper crucible, and the wall of the upper crucible may be tapered such that the bottom has a smaller area than an opening defined by a top edge of the walls.

In the system, the lower holder may engage an outer perimeter of the wall of the lower crucible, and the wall of the lower crucible may be tapered such that the bottom has a smaller area than an opening defined by a top edge of the walls.

The system may include a third holder for engaging another upper crucible or a lid An apparatus for testing material in a furnace is provided that includes a closed wall including an upper edge, a bottom edge and a continuous surface extending between the upper edge and the bottom edge. The apparatus also includes a bottom situated in an interior space of the wall and extending to the wall proximate to the bottom edge. The bottom forms with the closed wall a space adapted to enclose a first sample.

The apparatus also includes means for engaging a holder, and the apparatus is adapted to engage a lower crucible on an upper edge. The lower crucible has a closed wall and a bottom for enclosing a second sample.

In the apparatus, the means for engaging the holder may include at least one flange extending from an outside surface of the wall of the apparatus. The at least one flange may be adapted to engage a perimeter of an opening in the holder. In the apparatus, the at least one flange may extend around a circumference of an outside surface of the wall of the apparatus. The wall of the apparatus may be substantially vertical.

The wall of the apparatus may taper towards the bottom such that the bottom has a smaller area than an opening defined by the upper edge.

A method of testing samples in a furnace is provided that includes arranging a first sample in a lower crucible, arranging a second sample in a upper crucible, and determining a first weight of the first sample prior to heating. The method also includes stacking the upper crucible on the lower crucible, and determining a second weight of the second sample prior to heating. The method further includes determining a third weight of the first sample after heating, and determining a fourth weight of the second sample after heating.

The method may further include heating the upper crucible and the lower crucible in a furnace.

The operation of determining the first weight of the first sample prior to heating may include determining a lower crucible tare weight of the lower crucible, and determining a weight of the lower crucible with the first sample prior to heating. The operation of determining the first weight of the first sample prior to heating may also include subtracting the lower crucible tare weight from the weight of the lower crucible with the first sample to determine the first weight of the first sample prior to heating.

The operation of determining the second weight of the second sample prior to heating may includes determining an upper crucible tare weight of the upper crucible, and determining a weight of the upper crucible with the second sample stacked on the lower crucible with the first sample prior to heating. The operation of determining the second weight of the second sample prior to heating may also include subtracting the upper crucible tare weight and the weight of the lower crucible with the first sample from the weight of the upper crucible with the second sample stacked on the lower crucible with the first sample to determine the second weight of the second sample prior to heating.

In the method, the operation of determining the third weight of the first sample after heating may include determining a lower crucible tare weight of the lower crucible, and determining a weight of the lower crucible with the first sample after heating. The operation of determining the third weight of the first sample after heating may also include subtracting the lower crucible tare weight from the weight of the lower crucible with the first sample to determine the first weight of the first sample after heating. The operation of determining the fourth weight of the second sample after heating may include determining an upper crucible tare weight of the upper crucible, and determining a weight of the upper crucible with the second sample stacked on the lower crucible with the first sample after heating The operation of determining the fourth weight of the second sample after heating may also include subtracting the upper crucible tare weight and the weight of the lower crucible with the first sample from the weight of the upper crucible with the second sample stacked on the lower crucible with the first sample to determine the second weight of the second sample after heating.

In the method, the operation of determining the third weight of the first sample after heating may include repeatedly weighing the lower crucible with the first sample after a target temperature has been maintained for a minimum duration. The operation of determining the fourth weight of the second sample after heating may include repeatedly weighing the upper crucible with the second sample stacked on the lower crucible with the first sample after the target temperature has been maintained for the minimum duration.

A method of testing samples in a furnace is provided using upper and lower stackable crucibles. The method includes determining the weight of a combination of the upper and lower crucibles, and placing a sample in the upper crucible. The method also includes determining the weight of the sample prior to heating, and determining the weight of the sample after heating. In the method, the upper crucible has a first bottom area larger than a second bottom area of the lower crucible.

DETAILED DESCRIPTION OF THE INVENTION

Figure 1A:
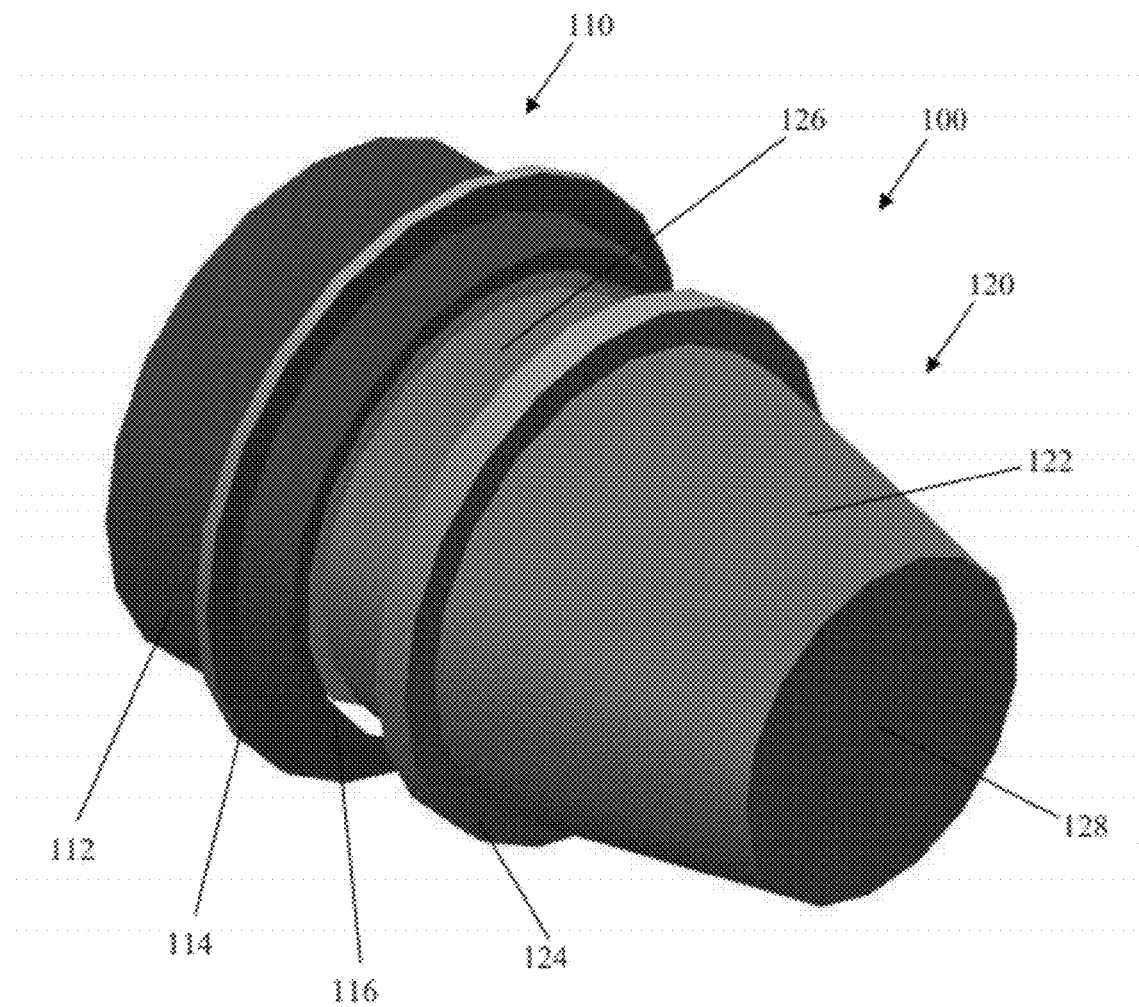
FIG. 1a is a perspective view of a crucible and container combination in accordance with an exemplary embodiment.

Thermogravimetric analyzers (TGA) operate to determine the moisture and/or ash in a sample. The container for testing a sample in a furnace is called a crucible or a container, and these terms are used interchangeably here. In particular, crucibles may be referred to as lower crucibles, and containers may be referred to as upper crucibles. An exemplary method using auto covers holding additional samples may include weighing the empty lower crucible and empty upper crucible, one after the other, to determine their tare weights. The tare of the upper crucible being the addition of the lower and the upper crucibles since the upper crucible sits on the lower crucible.

Subsequently, the upper crucible is removed and a sample is placed in the lower crucible, which is then weighed. The weighing is performed automatically and software determined. The upper crucible is placed on the lower crucible and the combination is weighed, which should correspond to the lower crucible with the sample and the upper crucible alone. Then a sample is put in the upper crucible and the combination is weighed to determine the weight of the upper crucible sample.

During furnace operations, the upper and lower crucibles are separated by the upper carousel and analysis is made only of the lower crucibles until constant weight is achieved on all the samples. This is accomplished by raising the upper carousel thereby lifting the upper crucible off of the lower crucible. Then the lower carousel is rotated so that the sample that is to be weighted is over the balance or scale within the furnace. Then the lower carousel is lowered so that the lower crucible rests on the scale unsupported by the lower carousel, and without the lower carousel itself resting on the scale. Then the weighing may be performed. Then the lower carousel is raised thereby lifting the lower crucible, and then the lower carousel may be rotated to position the next sample to be weighed. The upper carousel may rotate along with the lower carousel, and in most situations does rotate. However, since the upper carousel remains raised throughout the weighing of the lower crucibles, the upper crucible is not weighed. The weight of the sample may then be determined from the weight of the lower crucible and sample combination obtained and the weight of the lower crucible alone obtained initially.

Then the upper carousel is lowered onto the lower crucible and the total weight of the lower crucible and residue material enclosed therein is taken as the new tare weight of the lower crucible. The combination is then weighed, perhaps repeatedly, to obtain an average weight. The weight of the lower crucible and sample, and of the upper crucible, can be subtracted from the total weight to obtain the weight of the sample in the upper crucible.

In this manner, the capacity of the furnace is doubled and the weighing time is only increased slightly.

An upper and lower crucible combination may be used with a double carousel system as used in crucible cover systems, with little or no modifications to the upper carousel. An exemplary embodiment of the system may be used alternatively with crucible cover combinations and upper and lower crucible combinations.

In this manner, and when used with an upper and lower crucible combination, the capacity of the TGA may be doubled. A second specially designed crucible is used in an exemplary embodiment instead of the cover. In this case, only moisture and ash can be analyzed, since no cover is provided. However, it is possible to analyze several temperatures and other materials by raising the furnace temperature to the appropriate amount for an appropriate period of time, and then weighing the lower carousel crucibles, possibly repeatedly, until a constant weight is obtained for each lower crucible. Then the upper crucibles may be weighed, possibly repeatedly until a constant weight is obtained, subtracting the weight of the lower crucible and the material in the lower crucible. The temperature of the furnace may be maintained for a predetermined duration as controlled by the computer program. Alternatively or additionally, the temperature of the furnace may be maintained until a sample has achieved constant weight, in which constant weight may be defined as three consecutive weights of a same sample falling within a predetermined percentage of a sample original weight variation. For example, the percentage may be 0.02% variation per gram up to 1% variation per gram.

The weighing and calculating may be performed automatically by computer controlled systems. The temperatures that may be of interest in such a testing system include, for example 105, 300, 500, 800, and 1000 degrees Celsius.

The upper and lower crucibles do not need to form a seal of the space enclosing the sample in the lower crucible. Once the lower crucibles have constant weight, it is assumed that no more weight will be lost, and therefore now the upper crucibles may be weighed. The upper crucibles are lowered down to rest on top of the lower crucibles and the combination is weighed, perhaps repeatedly to determine a constant weight. Computer controlled carousels and robotic systems, as well as software managing the weighing system, may automatically calculate the weights of the samples given the tare weights of the upper and lower crucibles and the determined, constant weight of the lower crucible sample.

The method according to an exemplary embodiment may be summarized as follows. The lower and upper crucibles are initially weighed or tared, which entails first weighing all of the empty lower crucibles, then lowering the upper carousel holding all of the upper crucibles onto the lower crucibles, and then weighing the combination of the lower and upper crucibles. These steps may be taken automatically and the carousels and weighing instruments may be computer controlled and include software for determining the tare weights.

Then the lower crucible is loaded with material by removing the upper crucible and adding the sample. This operation may also be performed automatically or by hand. Then the weight of the lower crucible and sample is determined, which yields, through a simple subtraction of the weight of the empty lower crucible, the weight of the sample in the lower crucible. Then the upper crucible is placed in its position on top of the lower crucible, by for instance lowering an upper carousel, and then another sample is added of the upper crucible. The combination of the upper and lower crucible is weighed, which yields, through a simple subtraction of the weight of the empty upper crucible and the lower crucible and sample, the weight of the sample in the upper crucible.

All of these operations may be done by computer control driven by software, or by an operator's direct control, or manually.

The instrument then has a number of crucibles with sample in the upper and lower carousel, the instrument heats to a defined temperature and rotates and deposits crucibles (with the upper carousel raised) in the balance at regular intervals and looks for constant weight in the lower carousel crucibles, after all crucibles in the lower carousel reach constant weight the upper carousel lowers the upper crucibles on top of the lower carousel crucibles, since the lower carousel crucibles will not change in weight we can now look for constant weight in the sum of lower crucible, lower crucible sample, upper crucible and upper crucible sample, only one can change in weight and that is the upper crucible sample.

The upper crucible sample may achieve constant weight before the lower crucible sample reaches constant weight without negative consequence since all of the weights of the different components in the system are known. For instance, the original weight of lower and upper crucibles, without samples, is known. Additionally, the original sample weights in the lower and upper crucibles is also known. Finally, the final sample weight in lower crucible is known after weighing, possibly repeatedly. Therefore, the upper crucible sample may be weighed and the sample weight determined. For instance, if the upper crucible sample does not change, significantly, after being weighted three times, then the upper crucible sample weight may be determined with some confidence based on the three weights. For instance, the three weights may be averaged to determine a final weight for the upper crucible sample.

Alternatively, auto covers may be provided to the upper crucible, and a third carousel may be provided to handle this situation.

FIG. 1a is a perspective view of crucible and container combination 100 in accordance with an exemplary embodiment. Crucible and container combination 100 includes container 110 arranged to sit on top of, or rest on, crucible 120. Container 110 may include vertical sidewall 112 forming a substantially cylindrical shape. Flange 114 may extend outward from vertical sidewall 112, and may be continuous around a circumference of vertical sidewall 112, or may be interrupted. Vertical sidewall 112 may be substantially vertical or tapered. In the event that vertical sidewall 112 is tapered, it may be possible to omit flange 114 and to engage an upper carousel with vertical sidewall 112 directly. Bottom edge 116 of vertical sidewall 112 may engage crucible flange 124 of crucible 120 when container 110 is positioned to rest on crucible 120. Alternatively, upper edge 126 of crucible 120 may engage a bottom of container 110 when container 110 is positioned on crucible 120. A bottom of container 110 may be even with bottom edge 116, but more likely is positioned upward from bottom edge 116 to promote stability in the stacked arrangement. A bottom of container 110 may be even with flange 114, and may be structurally integrated or identical to flange 114.

Crucible 120 may include crucible sidewalls 122, which may be vertical or tapered, forming a substantially cylindrical or conical shape. Crucible 120 may also include bottom 128. A lower carousel may be adapted to engage crucible flange 124, or alternatively, where crucible sidewalls 122 are tapered, the lower carousel may engage crucible sidewalls 122 directly. In that case, if a bottom of container 110 is adapted to rest on upper edge 126 of crucible 120, flange 124 may be omitted from crucible 120. A seal may be formed between bottom edge 116 and crucible flange 124 or between a bottom of container 110 and upper edge 126 when container 110 is stacked on crucible 120.

Figure 1B:
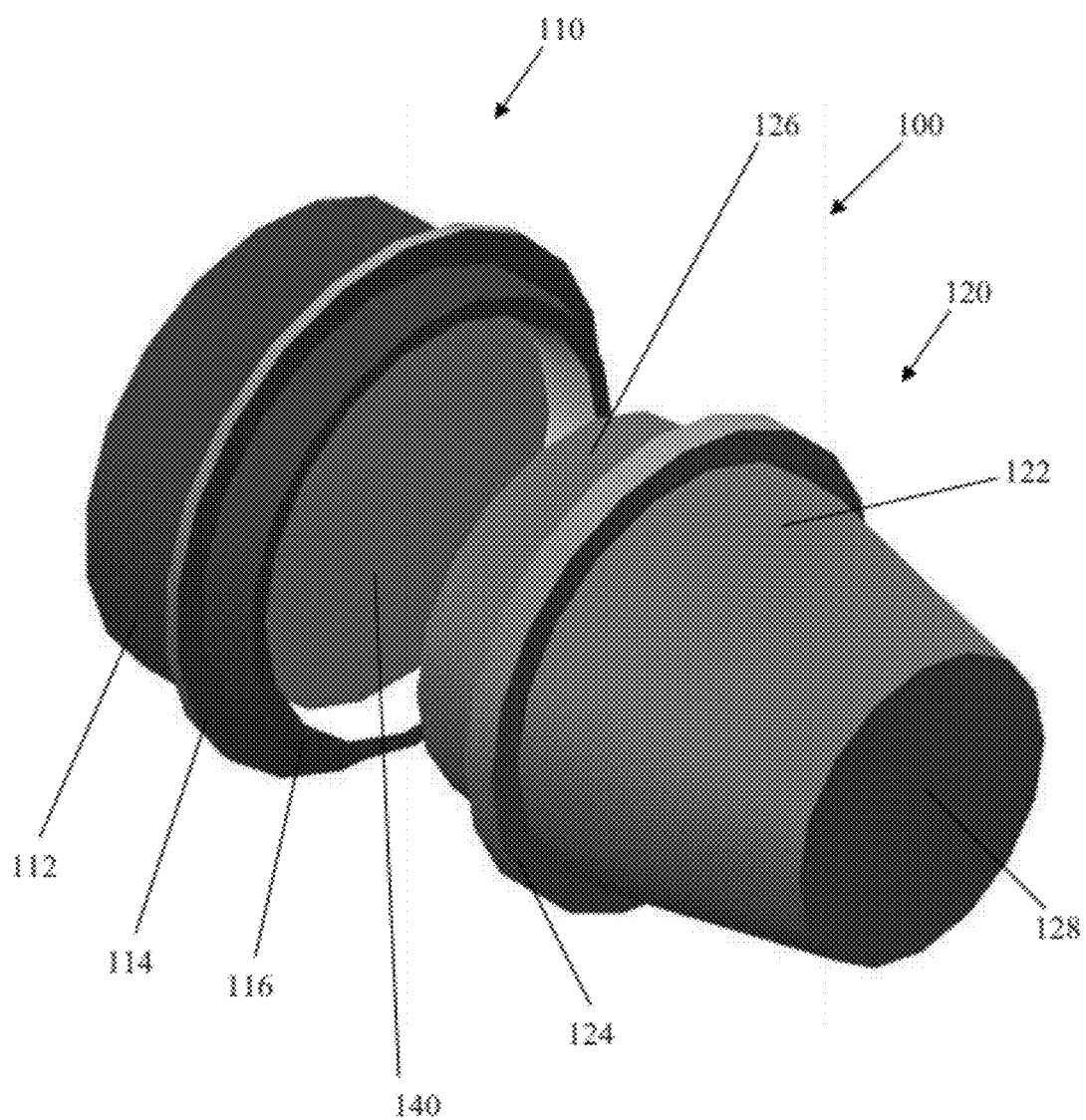
FIG. 1b is another perspective view of a crucible and container combination with the crucible and container separated in accordance with an exemplary embodiment.

FIG. 1b is another perspective view of crucible and container combination 100 in accordance with an exemplary embodiment, showing container 110 and crucible 120 separated. Container 110 includes vertical sidewall 112, flange 114 and bottom edge 116. Also visible in FIG. 1b is bottom 140 of container 110, which is recessed from bottom edge 116. Bottom 140 may be even with flange 114, and may be structurally integrated with flange 114. Crucible 120 includes crucible sidewalls 122, bottom 128, crucible flange 124, and upper edge 126.

Figure 1C:
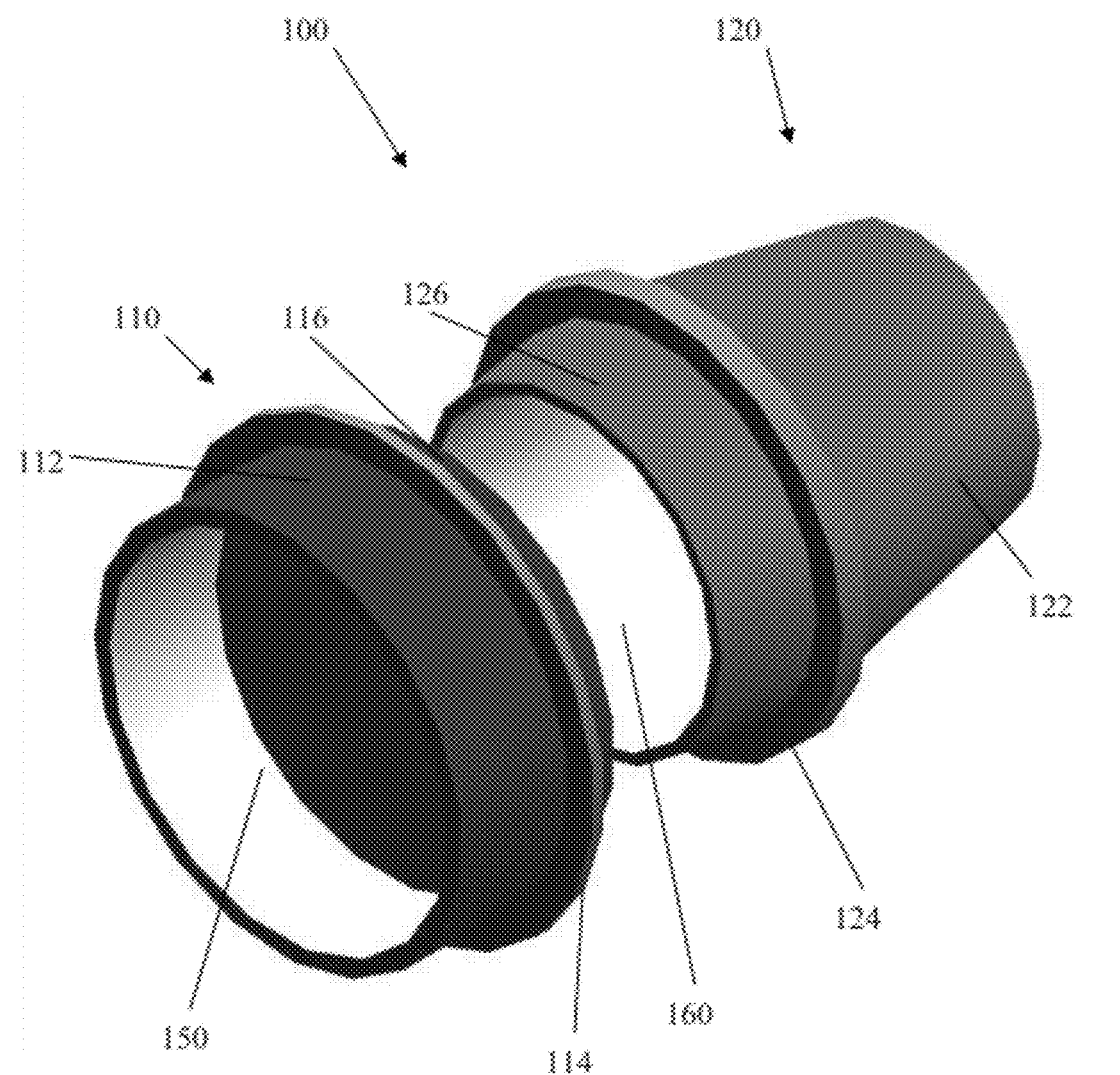
FIG. 1c is another perspective view of a crucible and container combination with the crucible and container separated in accordance with an exemplary embodiment.

FIG. 1c is another perspective view of a crucible and container combination 100 in accordance with an exemplary embodiment, showing container 110 and crucible 120 separated. Container 110 includes vertical sidewall 112, flange 114, and bottom edge 116. Also visible in FIG. 1c is interior space 150 of container 110, which is adapted to accommodate a material to be tested, for instance coal or coke. Crucible 120 includes crucible sidewalls 122, crucible flange 124, and upper edge 126. Also visible in FIG. 1c is interior space 160 of crucible 120, which is adapted to accommodate a material to be tested, for instance coal or coke.

The shape of container 110 may be modified to improve the efficiency of the weighing operation, and in particular may be adjusted to reduce the time required to complete the analysis. The time for a sample of moisture and ash to arrive at a constant weight is largely determined by the furnace temperature, the sample weight, the sample composition and the area of the sample exposed to the heat. The larger the area of the sample exposed to the heat, and therefore the thinner the sample layer for a specific sample weight, the shorter the analysis time. Since the temperature is set by standards, the sample weight is normally the same for specific samples, and the sample composition is the same for specific samples, the most significant variable to reduce the analysis time is the sample area subject to heat. The upper crucible, also referred to herein as container 110, may therefore be designed to have a large bottom area, as shown by bottom 140 in FIG. 1b.

Figure 2A:
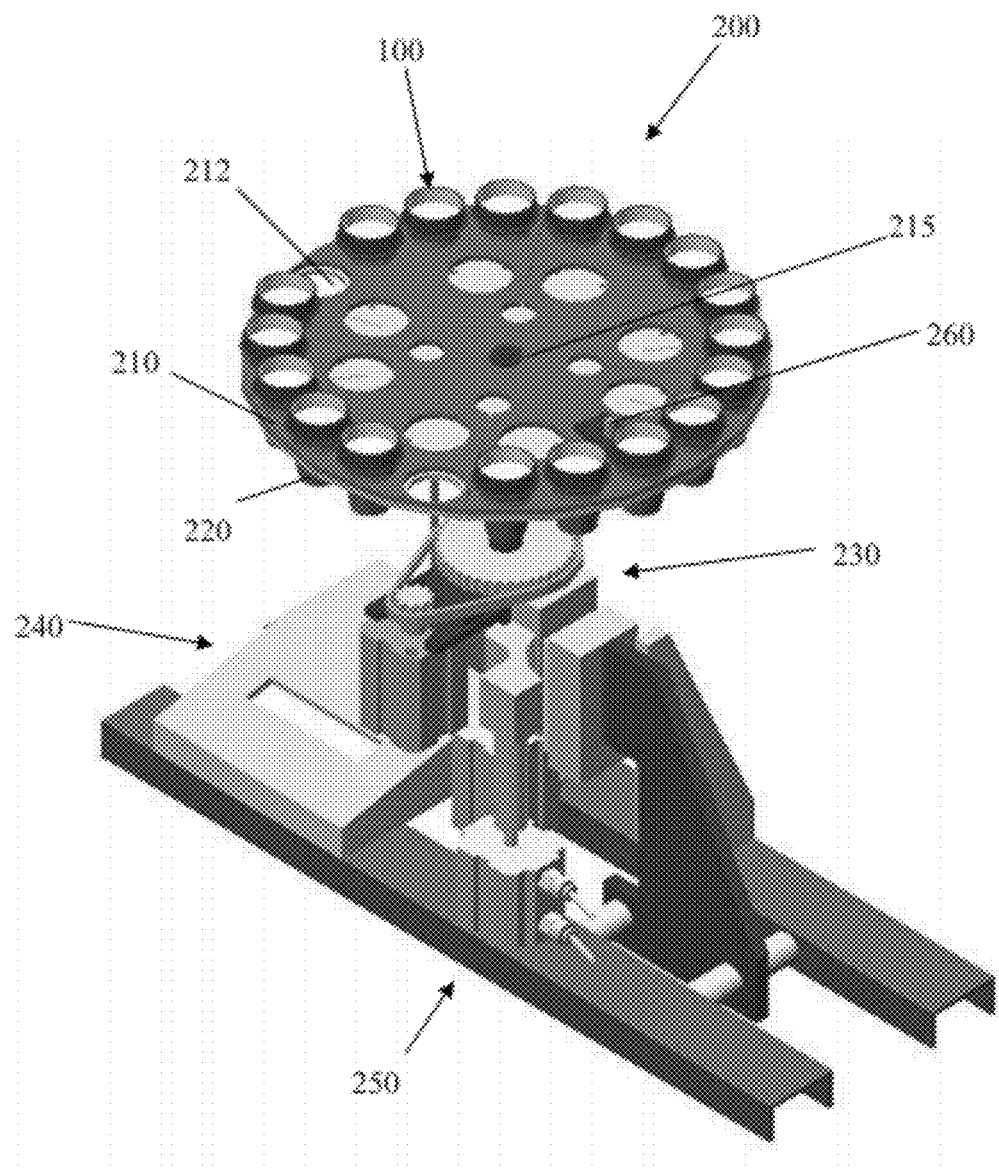
FIG. 2a is a perspective view of a carousel system including crucibles and containers in accordance with an exemplary embodiment.

In an exemplary method, container 110 may have a large bottom 140, in particular, larger than bottom 128 of crucible 120 bottom. Crucible and container combination 100 may be weighed empty, or tared, together and be used like a single crucible. In this manner, the analysis time may be reduced considerably due to the high surface area of the sample in the upper crucible exposed to the heat. The analysis time of the samples may be reduced by increasing sample surface area, thereby increasing productivity. Alternatively, the same arrangement may be used as discussed above using samples in both crucible 120 and container 110 of crucible and container combination 100, multiplying by two the number of samples tested. [Comment FIG. 2a is a perspective view of carousel system 200 including crucible and container combinations 100 in accordance with an exemplary embodiment. Upper carousel 210 and lower carousel 220 are arranged coaxially on axis 215. In FIG. 2a, upper carousel 210 and lower carousel 220 are together, and therefore a container of crucible and container combination 100 rests on a corresponding crucible of crucible and container combination 100.

Each of upper carousel 210 and lower carousel 220 has openings 212 with the openings 212 in lower carousel 220 being of a smaller diameter than openings 212 in upper carousel 210. Openings 212 are arranged around an outer perimeter and adapted to hold and engage one crucible and container combination 100. Upper carousel 210 and lower carousel 220 are able to move independent of each other, towards each other and away from each other, along axis 215. In this manner, when upper carousel 210 moves away from lower carousel 220, upper carousel 210 engages a container portion of crucible and container combination 100 and lower carousel 220 continues to engage a crucible of crucible and container combination 100. In particular, opening 212 in upper carousel 210 may have a diameter larger than the diameter of a crucible of crucible and container combination 100, and therefore when upper carousel 210 moves away from lower carousel 220, upper carousel 210 does not engage a crucible of crucible and container combination 100, which therefore lowers with lower carousel 220. Opening 212 in upper carousel 210 may have a diameter larger than the diameter of crucible 120 and flange 124 and smaller than diameter of flange 114 of container 110. Therefore when upper carousel 210 moves away from lower carousel 220, upper carousel 210 does engage a container of crucible and container combination 100. Opening 212 in lower carousel 220 may have a diameter smaller than the diameter of crucible 120 and flange 124 of crucible and container combination 100, and therefore lower carousel 220 engages crucible 120 of crucible and container combination 100 unless and/or until the crucible rests on another support, for example a balance or scale of scale 240.

Motor system 230 may operate to rotate upper carousel 210 and lower carousel 220, and may operate to move upper carousel 210 and lower carousel 220 together and up and/or down. Upper carousel 210 and lower carousel 220 may be turn freely and independently unless and until pin 260 is inserted through a hold in both upper carousel 210 and lower carousel 220, thereby attaching them to each other. In this manner, motor system 230 may cause upper carousel 210 and lower carousel 220 to move crucible and container combination 100 into position and to weigh a crucible of crucible and container combination 100 and/or crucible and container combination 100. A computer control system may connect to carousel system 200, motor system 230 and scale 240 via network connection 250. In this manner, a computer control system may weigh all of the samples in carousel system 200 and may store the weight data obtained from scale 240.

Figure 2B:
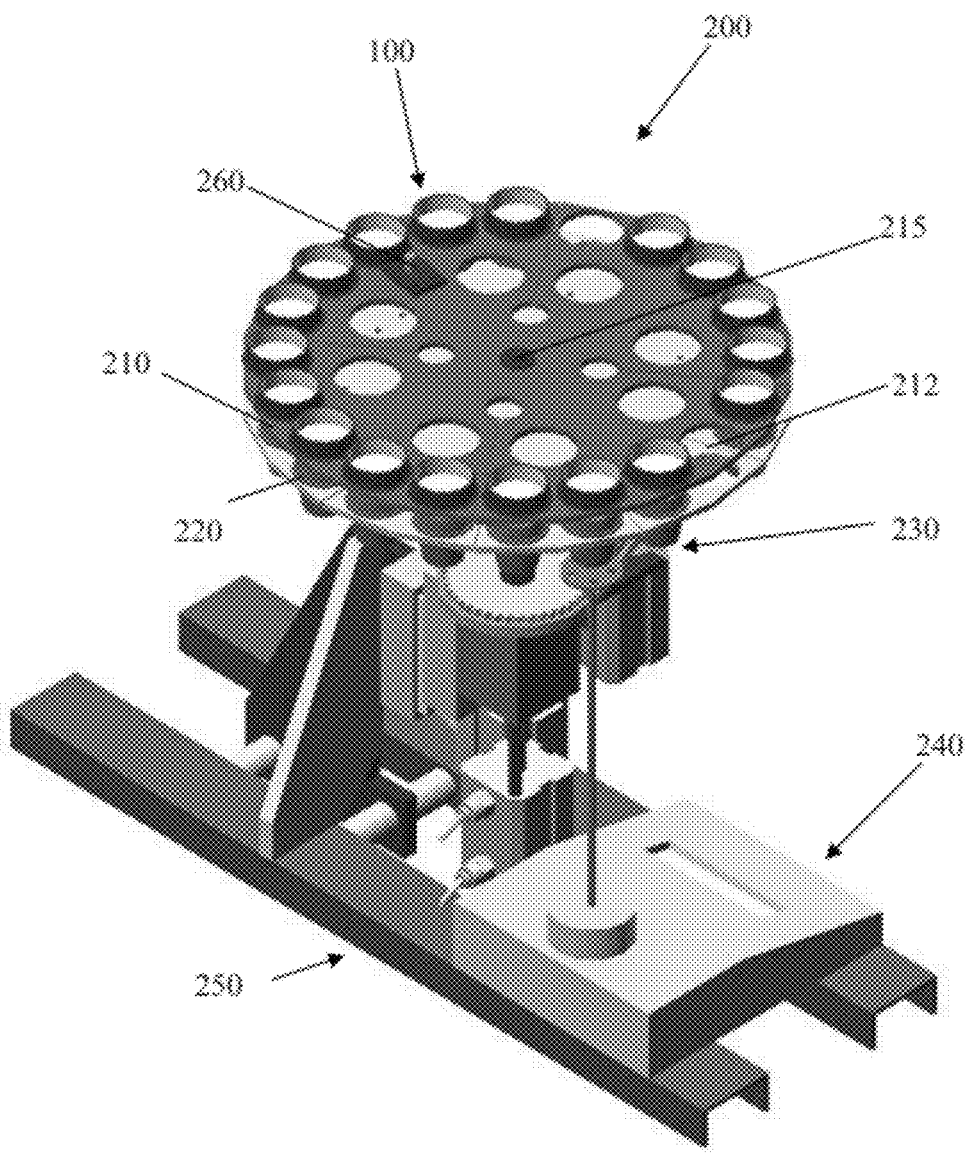
FIG. 2b is another perspective view of a carousel system including crucibles and containers in accordance with an exemplary embodiment.

FIG. 2b is another perspective view of carousel system 200 including crucible and container combinations 100 in accordance with an exemplary embodiment. In FIG. 2b, upper carousel 210 and lower carousel 220 are separated, and therefore a container of crucible and container combination 100 rests on upper carousel 210, while a corresponding crucible of crucible and container combination 100 rests on lower carousel 220. Also shown in FIG. 2b is scale 240.

Figure 3:
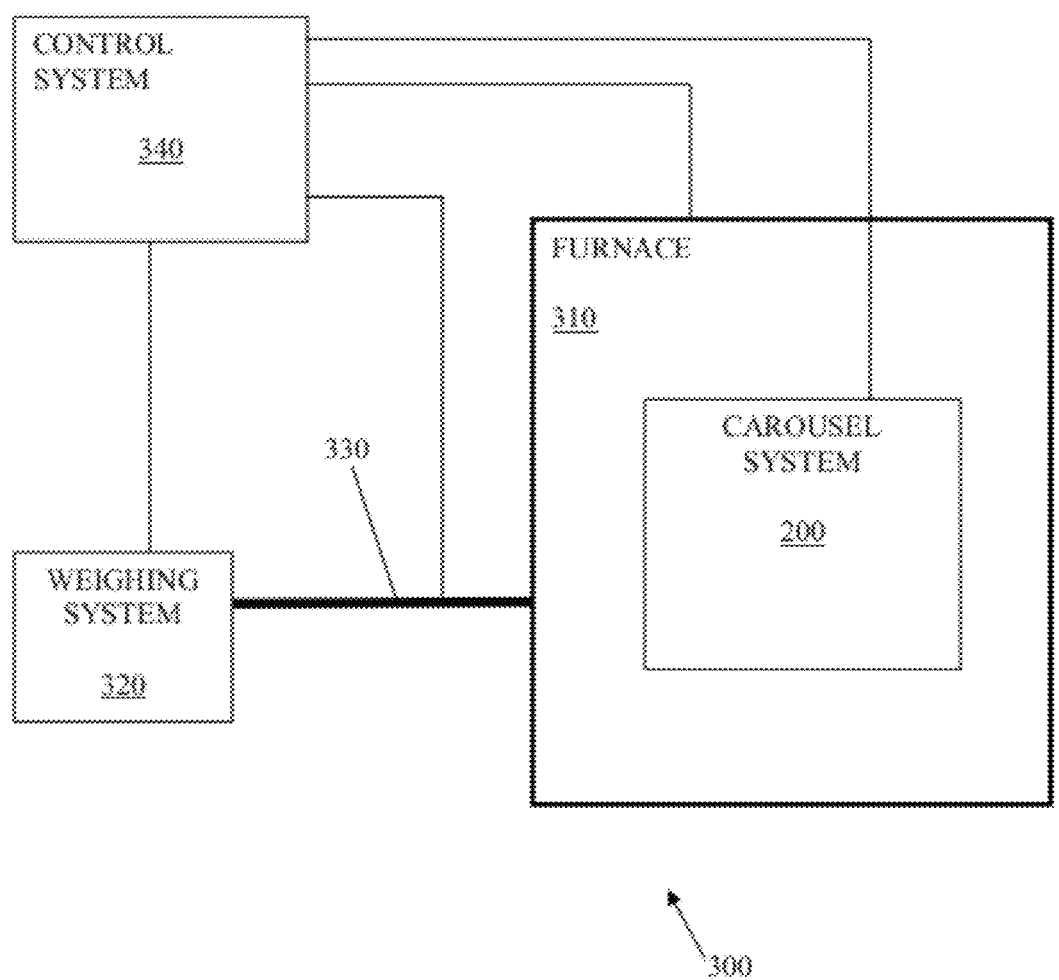
FIG. 3 is a schematic diagram of a system using crucibles and containers in accordance with an exemplary embodiment.

FIG. 3 is a schematic diagram of testing system 300 for analyzing moisture and/or ash in coal and/or coke samples. Testing system 300 includes furnace 310 which encloses carousel system 200. External to furnace 310 is weighing system 320, which may include a scale. Connecting weighing system 320 and furnace 310 in testing system 300 is moving system 330. Moving system 330 may include a robotic arm, a conveyor belt and/or any other appropriate mechanism for moving a container, a crucible, or a container and crucible combination. Weighing system 320, moving system 330, furnace 310 and carousel system 200 may all be electronically coupled to, and controlled by, control system 340. Control system 340 may include a computer, software, a network, and/or a cloud computing environment.

Figure 4:
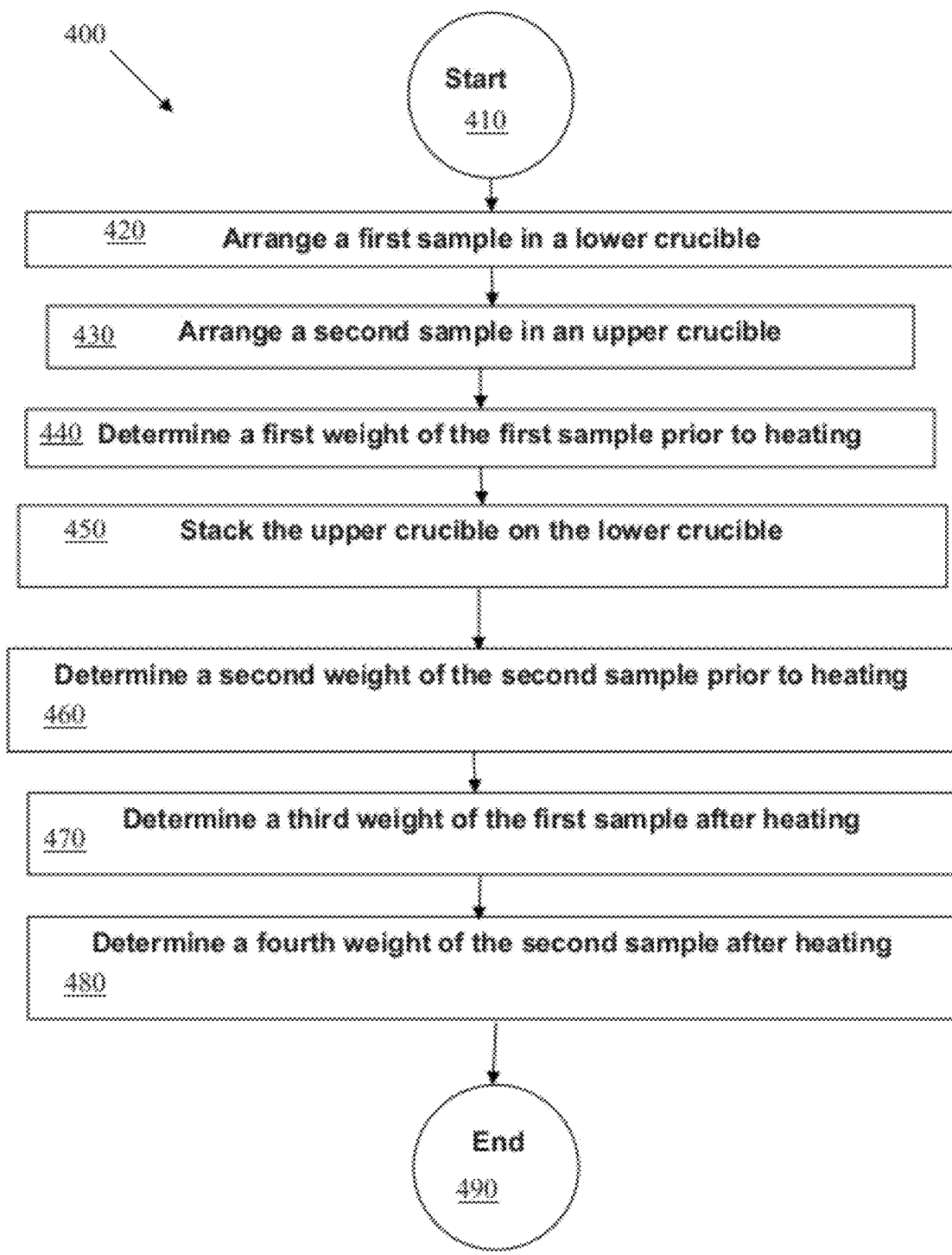
FIG. 4 illustrates a method according to an exemplary embodiment.

FIG. 4 illustrates method 400 according to an exemplary embodiment. Method 400 starts at start circle 410 and proceeds to operation 420, which indicates to arrange a first sample in a lower crucible. From operation 420 the flow in method 400 proceeds to operation 430, which indicates to arrange a second sample in an upper crucible. From operation 430 the flow in method 400 proceeds to operation 440, which indicates to determine a first weight of the first sample prior to heating. From operation 440 the flow in method 400 proceeds to operation 450, which indicates to stack the upper crucible on the lower crucible. From operation 450 the flow in method 400 proceeds to operation 460, which indicates to determine a second weight of the second sample prior to heating. From operation 460 the flow in method 400 proceeds to operation 470, which indicates to determine a third weight of the first sample after heating. From operation 470 the flow in method 400 proceeds to operation 480, which indicates to determine a fourth weight of the second sample after heating. From operation 480 the flow in method 400 proceeds to end circle 490.

In some methods, a sample may be only placed in the upper crucible, and the furnace system may only have one carousel. This arrangement may be useful in situations in which the upper crucible has a larger bottom area than the lower crucible, and using the upper crucible for sample testing purposes reduces testing time since a larger area of the sample is exposed to the air in the furnace, thereby reducing the amount of time necessary to bring the sample to equilibrium at a given temperature. In this arrangement, the upper and lower crucibles are tared together, and all weighing is done with both crucibles on the scale. Therefore, only one carousel is required to implement this method, and the single carousel would engage the lower crucible, while the upper crucible would rest on the lower crucible at all times.

Figure 5:
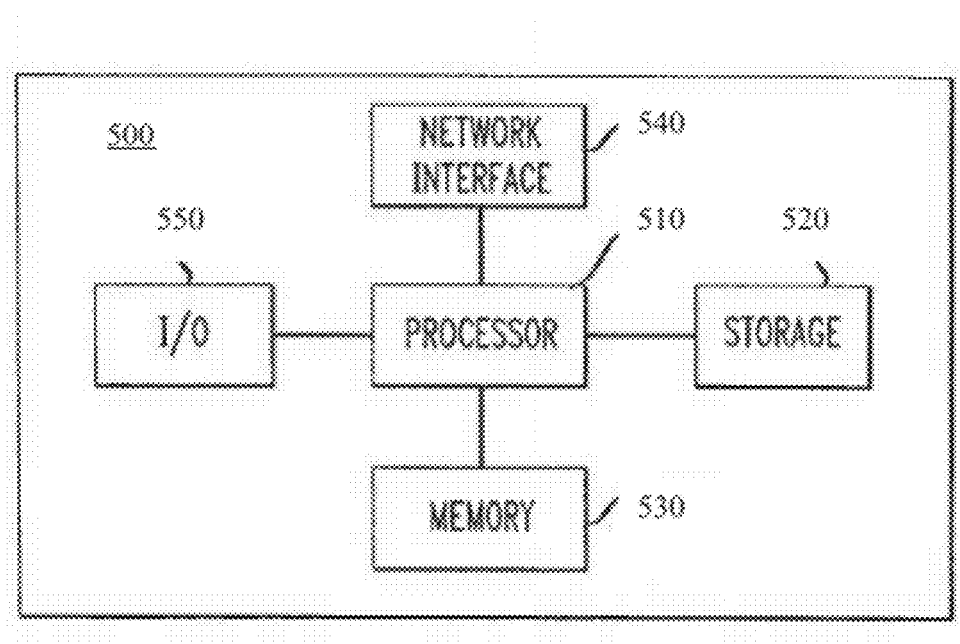
FIG. 5 illustrates a computer system according to an exemplary embodiment.

FIG. 5 illustrates a computer system according to an exemplary embodiment. Computer 500 can, for example, carousel system 200, motor system 230 and scale 240 via network connection 250, may control furnace 310, or may be control system 340. Additionally, computer 500 can perform the steps described above (e.g., with respect to FIG. 4). Computer 500 contains processor 510 which controls the operation of computer 500 by executing computer program instructions which define such operation, and which may be stored on a computer-readable recording medium. The computer program instructions may be stored in storage 520 (e.g., a magnetic disk, a database) and loaded into memory 530 when execution of the computer program instructions is desired. Thus, the computer operation will be defined by computer program instructions stored in memory 530 and/or storage 520 and computer 500 will be controlled by processor 510 executing the computer program instructions. Computer 500 also includes one or more network interfaces 540 for communicating with other devices, for example other computers, servers, or websites. Network interface 540 may, for example, be a local network, a wireless network, an intranet, or the Internet. Computer 500 also includes input/output 550, which represents devices which allow for user interaction with the computer 500 (e.g., display, keyboard, mouse, speakers, buttons, webcams, etc.). One skilled in the art will recognize that an implementation of an actual computer will contain other components as well, and that FIG. 5 is a high level representation of some of the components of such a computer for illustrative purposes.

While only a limited number of preferred embodiments of the present invention have been disclosed for purposes of illustration, it is obvious that many modifications and variations could be made thereto. It is intended to cover all of those modifications and variations which fall within the scope of the present invention, as defined by the following claims.

I claim:

1. A system for analyzing a plurality of samples in a furnace, comprising:
    an upper holder comprising at least one opening adapted to engage at least one upper crucible, each upper crucible being adapted to retain a first sample;
    a lower holder comprising at least one opening adapted to engage at least one lower, crucible, each lower crucible being adapted to retain a second sample;
    a scale adapted to receive and weigh the lower crucible, the scale further adapted to receive and weigh a combination of an upper crucible stacked on the lower crucible;
    a furnace enclosing the upper holder, the lower holder and the scale; and
    means for moving the upper holder and the lower holder relative to each other between a first position wherein the upper and lower crucibles are remote and a second position wherein the upper crucible is stacked on the lower crucible, and for moving the lower crucible or the combination of the upper crucible stacked on the lower crucible relative to the scale so that the scale receives and weights either the lower crucible or the combination of the upper crucible stacked on the lower crucible.

2. The system of claim 1, wherein:
    the upper holder is an upper carousel and the lower holder is a lower carousel;
    the upper carousel and the lower carousel are coaxial; and
    the upper carousel and the lower carousel rotate together.

3. The system of claim 2, wherein the means for moving the upper holder and the lower holder relative to each other and relative to the scale comprises means for moving at least one of the upper carousel and the lower carousel rotate axially with respect to the other of the upper carousel and the lower carousel.

4. The system of claim 2, wherein:
    the openings of the upper carousel are positioned away from a central axis; and
    the openings of the lower carousel are positioned away from the central axis and are aligned vertically with the openings of the upper carousel.

5. The system of claim 4, wherein:
the openings of the upper carousel are positioned around an outer edge of the upper carousel; and
the openings of the lower carousel are positioned around an outer edge of the lower carousel.

6. The system of claim 1, wherein:
the upper crucible comprises a wall and a bottom for enclosing a first sample;
the upper holder engages one of an outer perimeter of the wall of the upper crucible and a flange on the outer perimeter of the wall of the upper crucible;
the lower crucible comprises a wall and a bottom for enclosing a second sample;
the lower holder engages one of an outer perimeter of the wall of the lower crucible and a flange on the outer perimeter of the wall of the lower crucible.

7. The system of claim 1, wherein:
the upper holder engages an outer perimeter of the wall of the upper crucible;
the wall of the upper crucible is tapered such that the bottom has a smaller area than an opening defined by a top edge of the walls.

8. The system of claim 1, wherein:
the lower holder engages an outer perimeter of the wall of the lower crucible;
the wall of the lower crucible is tapered such that the bottom has a smaller area than an opening defined by a top edge of the walls.

9. The system of claim 1, further comprising a third holder for engaging one of another upper crucible and a lid.

10. A method of testing samples in a furnace using upper and lower stackable crucibles, comprising:
placing a first sample in the lower crucible;
placing a second sample in the upper crucible;
determining the weight of the first sample prior to heating;
stacking the upper crucible on the lower crucible;
determining the weight of the second sample prior to heating;
determining the weight of the first sample after heating; and
determining the weight of the second sample after heating.

11. The method of claim 10, further comprising heating the upper crucible and the lower crucible in a furnace.

12. The method of claim 10, wherein the operation of determining the weight of the first sample prior to heating comprises:
determining a lower crucible tare weight of the lower crucible;
determining the weight of the lower crucible with the first sample prior to heating; and
subtracting the lower crucible tare weight from the weight of the lower crucible with the first sample to determine the weight of the first sample prior to heating.

13. The method of claim 12, wherein the operation of determining the weight of the second sample prior to heating comprises:
determining an upper crucible tare weight of the upper crucible;
determining the weight of the upper crucible with the second sample stacked on the lower crucible with the first sample prior to heating; and
subtracting the upper crucible tare weight and the weight of the lower crucible with the first sample from the weight of the upper crucible with the second sample stacked on the lower crucible with the first sample to determine the weight of the second sample prior to heating.

14. The method of claim 10, wherein:
the operation of determining the weight of the first sample after heating comprises:
determining a lower crucible tare weight of the lower crucible;
determining the weight of the lower crucible with the first sample after heating; and
subtracting the lower crucible tare weight from the weight of the lower crucible with the first sample to determine the weight of the first sample after heating; and
the operation of determining the weight of the second sample after heating comprises:
determining an upper crucible tare weight of the upper crucible;
determining the weight of the upper crucible with the second sample stacked on the lower crucible with the first sample after heating; and
subtracting the upper crucible tare weight and the weight of the lower crucible with the first sample from the weight of the upper crucible with the second sample stacked on the lower crucible with the first sample to determine the weight of the second sample after heating.

15. The method of claim 10, wherein:
the operation of determining the weight of the first sample after heating comprise repeatedly weighing the lower crucible with the first sample after a target temperature has been reached and until a constant weight is obtained; and
the operation of determining the fourth weight of the second sample after heating comprises repeatedly weighing the lower crucible with the first sample after a target temperature has been reached and until a constant weight is obtained.

16. A method of testing samples in a furnace using upper and lower stackable crucibles, comprising:
determining the weight of a combination of the upper and lower crucibles;
placing a sample in the upper crucible;
determining the weight of the sample prior to heating; and
determining the weight of the sample after heating;
wherein the upper crucible has a first bottom area larger than a second bottom area of the lower crucible.

* * * * *